United States Patent

De Buck

[11] Patent Number: 5,678,997
[45] Date of Patent: Oct. 21, 1997

[54] DENTURE ATTACHMENT SYSTEM

[75] Inventor: Vincent De Buck, Sint Niklaas, Belgium

[73] Assignee: Ceka N.V., Antwerp, Belgium

[21] Appl. No.: 496,477

[22] Filed: Jun. 29, 1995

[30] Foreign Application Priority Data

Jun. 29, 1994 [DE] Germany .......... 44 22 773.6

[51] Int. Cl.⁶ .......... A61C 13/12; A61C 13/225
[52] U.S. Cl. .......... 433/177; 433/181
[58] Field of Search .......... 433/177, 172, 433/181, 182, 183

[56] References Cited

U.S. PATENT DOCUMENTS

| | | | |
|---|---|---|---|
| 1,140,537 | 5/1915 | Skinner | 433/177 |
| 1,297,561 | 3/1919 | Guntner | 433/181 |
| 4,209,904 | 7/1980 | Staubli | 433/177 |
| 4,362,509 | 12/1982 | Sulc | 433/181 |
| 4,661,068 | 4/1987 | Harrison | 433/181 |
| 5,417,570 | 5/1995 | Zuest et al. | 433/177 |

FOREIGN PATENT DOCUMENTS

| | | | |
|---|---|---|---|
| 473993 | 3/1992 | European Pat. Off. | 433/177 |
| 1516457 | 1/1970 | Germany . | |
| 597843 | 11/1977 | Switzerland . | |

*Primary Examiner*—Nicholas D. Lucchesi
*Attorney, Agent, or Firm*—Herbert Dubno

[57] ABSTRACT

An attachment system for securing to a mounting bar a denture having a plastic base formed with a groove. The system has a generally C-section plastic rider engaged over the bar, having an outer surface with a predetermined outside cross-wise dimension, and engaged in the groove. An elastically deformable liner element of a material substantially harder than the plastic of the rider and of the base is imbedded in the base and forms an inner surface of the groove engaging the outer surface of the rider. The liner element defines a mouth opening having an inside width slightly Smaller than the outside cross-wise dimension of the rider so that the rider can only move into and out of the groove with deformation of the rider and/or of the liner element.

8 Claims, 2 Drawing Sheets

DENTURE ATTACHMENT SYSTEM

FIELD OF THE INVENTION

The present invention relates to a denture attachment system. More particularly this invention concerns a system for securing a nonpermanent dental prosthesis to a denture bar or the like.

BACKGROUND OF THE INVENTION

A standard dental prosthesis is secured to a bar that is mounted in the mouth, typically with the ends of the bar secured in implanted anchors, in vital teeth, or nonvital roots, with the bar extending along and above the gum line where teeth are missing. This bar is typically made by investment casting and is ground and/or polished by hand, then fitted to the patient.

The denture itself normally has a gum or base part cast from a durable plastic and teeth that may be of another plastic or ceramic material. The base part of the denture is formed with a groove adapted to fit over the bar and of precise internal dimensions that are substantially greater than the outside dimensions of the bar. So-called riders which are plastic C-section channels are fitted to the bar. The inside dimensions of the riders correspond to the outside diameter of the normally circular-section bar and the outside dimensions correspond to the inside dimensions of the upper part of the groove. Such a system is described in Swiss patent 597,843 of H. Hader and the use of similar riders to attach partial dentures is described in U.S. Pat. No. 4,661,068 of J. Harrison.

The riders function primarily to adapt the dimensions of the bar to the dimensions of the denture groove. Thus they are available in different inside diameters. In addition they are replaceable so that, as the denture gets loose, the riders can be stripped from it and replaced to tighten the assembly.

Even though the denture base is formed of a hard and durable plastic, the groove will normally wear with time. As it gets bigger even new riders will not fit tightly, requiring preparation of a new appliance. It has been suggested by the Hader company to cast the denture base of metal, which will indeed reduce wear, but this creates a heat-sensitive and problematic appliance.

It has also been proposed in German patent document 1,516,457 of G. Wittenhagen and in the system of Servo-Dental to line the groove with a cast U-shaped metal element of precise dimensions. While this seems to offer a logical wear-resistant solution, in practice it often does not provide a tight fit from the beginning. If the bar is, for example, a little undersized, the normally resilient rider will clench it tightly and will be of outside dimensions that are somewhat less than desired or will sit loosely on the bar, so that the fit will be loose. Alternately if the bar is somewhat oversized, the rider will be spread and its outside dimensions will be greater than intended, making it a very tight or impossible fit in the metal liner.

OBJECTS OF THE INVENTION

It is therefore an object of the present invention to provide an improved denture attachment system.

Another object is the provision of such an improved denture attachment system which overcomes the above-given disadvantages, that is which is highly wear resistant but which nonetheless is capable of accommodating bars and riders of different dimensions.

SUMMARY OF THE INVENTION

An attachment system for securing to a mounting bar a denture having a plastic base formed with a groove has according to the invention a generally C-section plastic rider engaged over the bar, having an outer surface with a predetermined outside cross-wise dimension, and engaged in the groove. An elastically deformable liner element of a material substantially harder than the plastic of the rider and of the base is imbedded in the base and forms an inner surface of the groove engaging the outer surface of the rider. The liner element defines a mouth opening having an inside width slightly smaller than the outside cross-wise dimension of the rider so that the rider can only move into and out of the groove with deformation of the rider and/or of the liner element.

The use of an elastically resilient liner element means that the liner will perfectly fit the rider even if the bar is somewhat oversized or undersized. The denture is constructed by fitting a fabricating rider over the bar, fitting the liner element over the fabricating rider, then casting the denture base. If the bar is somewhat undersized the resilient liner element will compress the rider into a snug fit and will be cast in this position, ensuring a perfect fit. Similarly if the bar is somewhat oversized the resilient rider and the liner element will be spread and then this spread position will be fixed when it is cast into the tooth base. Thus the use of an elastically resilient liner element provides substantial advantages in addition to providing a wear-resistant surface in the denture-base groove.

According to the invention the rider outer surface lies flatly and complementarily against the inner surface of the liner element. In addition the liner element is generally $\Omega$-shaped and has a pair of radially outwardly projecting legs substantially wholly imbedded in the base. The liner element is spring steel, having a thickness of between 0.15 mm and 0.2 mm. The steel is stainless steel, preferably INOX 316L.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
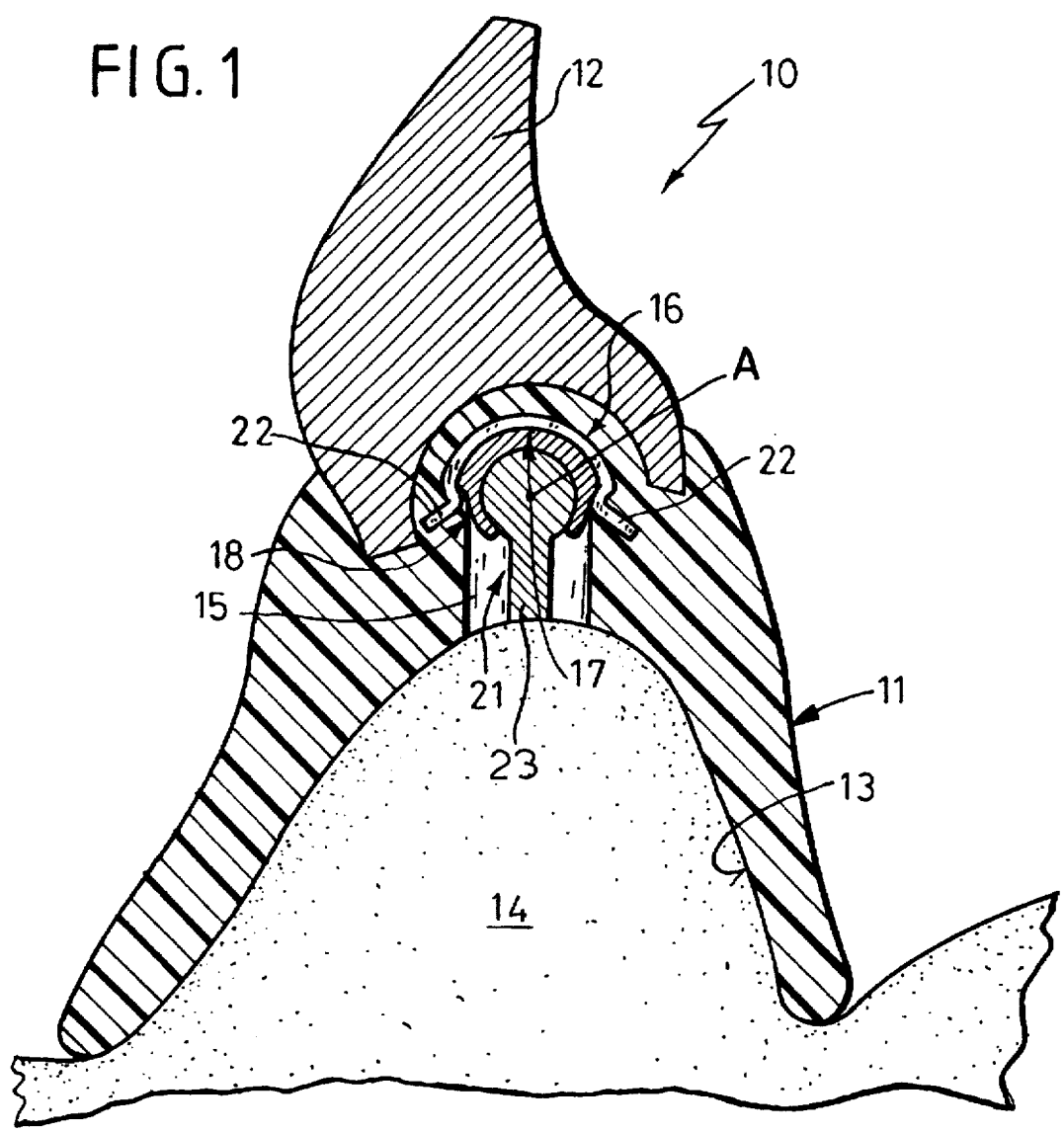
FIG. 1 is a vertical cross section through a denture mounted with the system of this invention.
Figure 2:
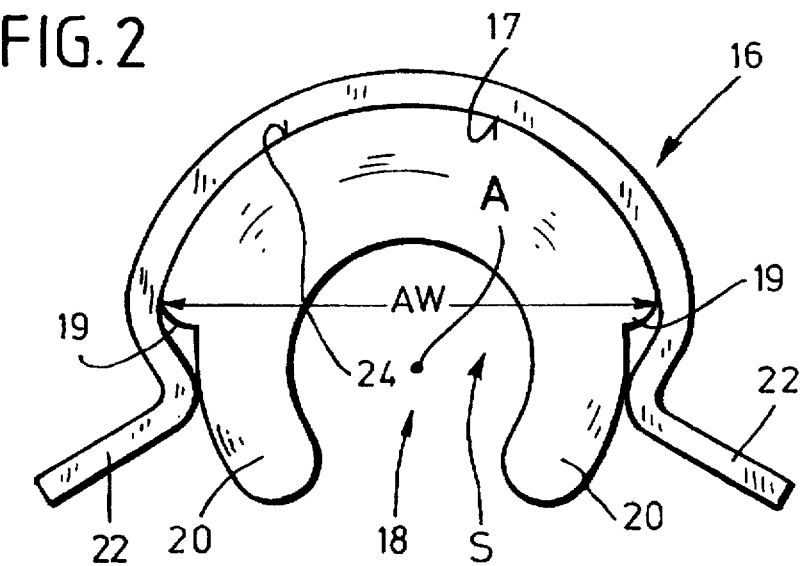
FIG. 2 is a large-scale vertical end view of the rider and liner element of this invention.

As seen in FIG. 1 a denture 10 is basically comprised of a base part 11 formed of a durable synthetic resin and a tooth part 12 of a harder material. The base part 11 is formed with a downwardly open cavity 13 adapted to fit over a gum region 14. A bar 21 of circular section is secured relative to the gums 14, normally with its end mounted in implant anchors 23 or adjacent teeth or tooth roots.

Figure 3:
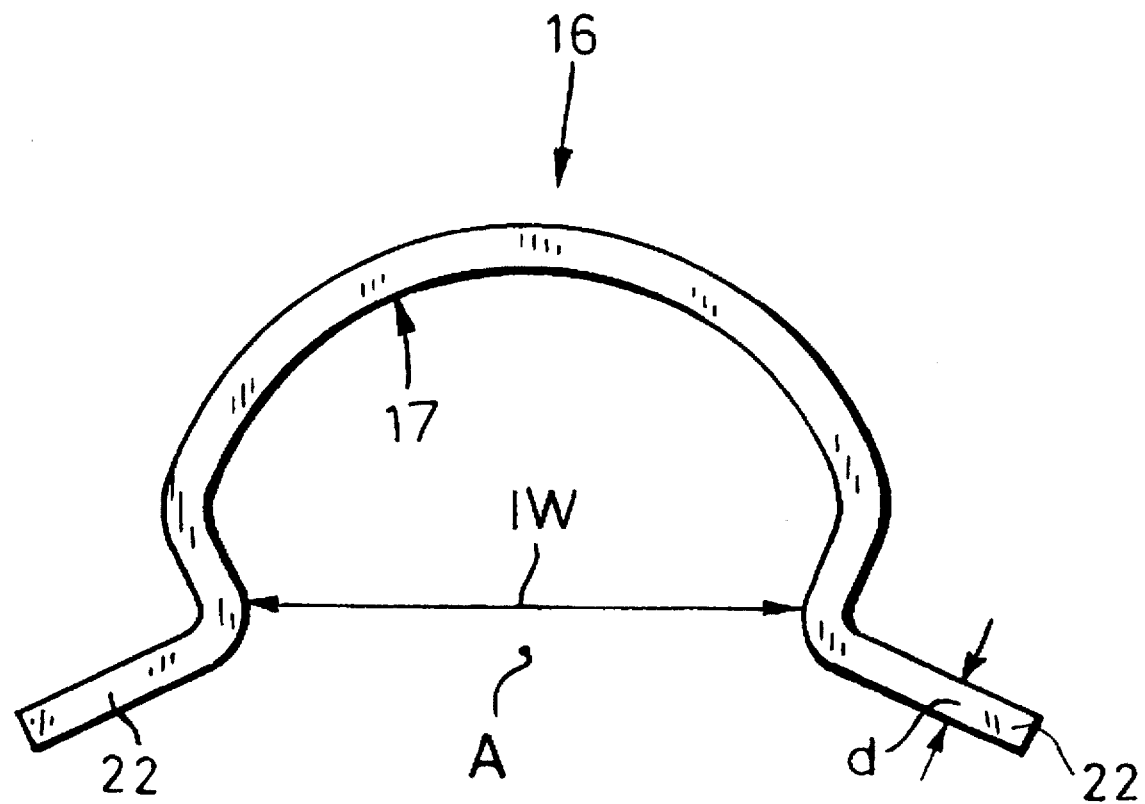
FIG. 3 is a large-scale end view of the liner element.

The prosthesis 10 is formed with a downwardly open groove 15 along which the bar 21 runs and which is coaxial along a central axis A of the bar 21. The upper region of this groove 15 is lined with an $\Omega$-section channel-shaped liner element 16 having a pair of radially extending legs 22 that are imbedded in the denture base 11 and an inner surface 17 of part-cylindrical shape. The liner element 16 is made of Inox 316L stainless steel and has a thickness d (FIG. 3) of between 0.15 mm and 0.2 mm.

The bar 21 carries a conventional rider 18 of the type described in above-cited Swiss patent 597,843 that is made of a durable plastic and that has a pair of legs 20 that grip around the bar 21 and a pair of shoulders 19 defining an outside dimension AW that is substantially more than an inside dimension IW defined by the mouth of the Ω-shaped liner 16. The rider 18 has a part-cylindrical outer surface 24 that complementarily fits with the inner surface 17 of the liner 16.

The prosthesis 10 is made by fitting over the bar 21 a fabricating rider having a top identical to the rider 18 but a pair of long legs and then clipping over it the liner 16, or even a plurality of such liners 16 in some situations. Since the liner 16 is highly elastically deformable it will conform to the shape of the rider even if same is spread somewhat by being forced over an oversized bar 21 or is somewhat smaller than normal because it is fitting over an undersized bar 21. Either way when the part 11 is molded around it, imbedding the legs 22, the shape and position of the liner 16 will be set.

During subsequent use with some inevitable rocking of the denture 10 relative to the gums 14, the wear will be wholly concentrated in the rider 18, since both the metallic liner 16 and bar 21 are much harder. As this rider 18 is intended to be replaced periodically, such wear is no problem.

I claim:

1. In combination with a mounting bar and a denture having a plastic base formed with a groove, an attachment system comprising:

a generally C-section plastic rider engaged over the bar, having an outer surface with a predetermined outside cross-wise dimension and an inner surface, and engaged in the groove; and an elastically deformable liner element of a material substantially harder than the plastic of the rider and of the base, imbedded in the base, forming an inner surface of the groove engaging the outer surface of the rider, and elastically pressing the inner surface of the rider against the mounting bar, the liner element defining a mouth opening having an inside width slightly smaller than the outside cross-wise dimension of the rider, the rider being movable through the mouth opening into and out of the groove with elastic deformation of the rider and/or of the liner element.

2. The attachment system defined in claim 1 wherein the rider outer surface lies flatly and complementarily-against the inner surface of the liner element.

3. The attachment system defined in claim 1 wherein the liner element is generally Ω-shaped and has a pair of radially outwardly projecting legs substantially wholly imbedded in the base.

4. The attachment system defined in claim 1 wherein the material of the liner element is spring steel.

5. The attachment system defined in claim 4 wherein the liner element has a thickness of between 0.15 mm and 0.2 mm.

6. The attachment system defined in claim 4 wherein the steel is stainless steel.

7. The attachment system defined in claim 6 wherein the steel is INOX 316L.

8. The attachment system defined in claim 1 wherein the inner and outer surfaces are complementarily part cylindrical.

* * * * *